US00PP23324P2

(12) United States Plant Patent
Bédard

(10) Patent No.: US PP23,324 P2
(45) Date of Patent: Jan. 15, 2013

(54) MINIATURE ROSE PLANT NAMED 'WEKCOFBUNK'

(50) Latin Name: *Rosa hybrida*
Varietal Denomination: WEKcofbunk

(75) Inventor: Christian Bédard, Brea, CA (US)

(73) Assignee: Weeks Roses, Pomona, CA (US)

( * ) Notice: Subject to any disclaimer, the term of this patent is extended or adjusted under 35 U.S.C. 154(b) by 0 days.

(21) Appl. No.: 13/373,164

(22) Filed: Nov. 7, 2011

(51) Int. Cl.
*A01H 5/00* (2006.01)

(52) U.S. Cl. ..... Plt./119

(58) Field of Classification Search ..... Plt./119
See application file for complete search history.

*Primary Examiner* — June Hwu
*Assistant Examiner* — Louanne Krawczewicz Myers
(74) *Attorney, Agent, or Firm* — McKee, Voorhees & Sease, P.L.C.

(57) ABSTRACT

A new variety of Miniature rose suitable for garden decoration, having flowers of twinkling brilliant orange coloration.

1 Drawing Sheet

Classification: The present invention relates to a new *Rosa hybrida* plant.

Variety denomination: The new plant has the varietal denomination 'WEKcofbunk'.

BACKGROUND OF THE INVENTION

This invention relates to a new and distinct variety of Miniature Rose. It has as its seed parent the variety known as 'WEKdoudou' (U.S. Plant Pat. No. 20,345) and an unknown pollen parent.

SUMMARY OF THE INVENTION

Among the features which distinguish the new variety from other presently available and commercial rose cultivars known to the inventor are the following combinations of characteristics: its unusual twinkling brilliant orange coloration, its excellent color stability throughout the life of the flower and its bushy upright tall growing habit for the class. The plant has a bushy upright growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKcofbunk' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'WEKdoudou' by the following combination of characteristics: whereas 'WEKcofbunk' bears semi-double flowers (about 12 to 17 petals) of twinkling brilliant orange coloration, 'WEKdoudou' bears semi-double flowers of smoky chocolate orange with a rust reverse coloration with significantly lesser petalage (about 5 to 10 petals). The new variety has a bushy upright tall growing habit (about 90 to about 110 cm. in height), whereas the seed parent has a bushy compact rounded significantly shorter growing habit (about 42 to about 52 cm. in height).

The pollen parent is unknown.

COMPARISON WITH THE CLOSEST COMMERCIALLY AVAILABLE CULTIVAR

The new variety may be distinguished from its closest commercially available cultivar, 'POUltop' (U.S. Plant Pat. No. 9,048) by the following combination of characteristics: whereas 'WEKcofbunk' bears somewhat large (about 5.4 to about 6.9 cm. in diameter) semi-double flowers (about 12 to 17 petals), 'POUltop' bears smaller flowers (ranging from 4 to 6 cm. in diameter) with significantly heavier petalage (18 to 22 petals). The new variety has a bushy upright tall growing habit (about 90 to about 110 cm. in height), whereas the closest commercially available cultivar has a dwarf, bushy, compact, significantly shorter growing habit (about 40 to 60 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The following photograph illustrates a 3 to 4 year-old rose plant of the new variety grown outdoors in Wasco, Calif. in the month of October. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, Calif. in the month of October. Phenotypic expression may vary with environmental, cultural and climatic conditions, as well as differences in conditions of light and soil.

FLOWER

The new variety sometimes bears its flowers singly, sometimes in clusters of two to four per stem. Flowers may be borne in regular rounded clusters on strong short to medium length stems (about 11 to about 34 cm.). Outdoors, the plant blooms abundantly and nearly continuously during the growing season. The flowers have a very slight tea fragrance.

BUD

The peduncle is about 1.9 to about 5.5 cm. in length, of average to somewhat heavy caliper (about 0.2 to about 0.3 cm. in diameter), and usually erect. It is moderately rough, with many stipitate glands. Peduncle color is between 146B and 146A often heavily suffused, especially on the side exposed to the sun, with between 187B and 183B.

Before the calyx breaks, the bud is about 1.0 to about 1.3 cm. in diameter at the widest point, about 1.2 to about 1.7 cm. in length, and pointed to somewhat ovoid in shape with a conspicuous neck. The surface of the bud bears between 13 to 15 foliaceous appendages and many stipitate glands, usually with slender entire foliaceous parts extending beyond the tip of the bud about ½ or more of its length. Bud color is between 146A and 146B often heavily suffused, especially on the side exposed to the sun, with between 187B and 183A.

The sepals are about 1.8 to about 3.0 cm. in length and about 0.6 to about 0.9 cm. in width at the widest point. The outer surface color of the sepal is between 146A and 146B often heavily suffused, especially on the side exposed to the sun, with between 187B and 183A. The outer surface texture of the sepal is moderately rough with many stipitate glands. The inner surface color of the sepal is near 146B broadly bordered by near 139A. After the sepals open, the inner surface color is often heavily suffused, especially on the area exposed to the sun, with between 187A and 187B. The inner surface of the sepal is covered with fine wooly tomentum; sepal margins are lined with few stipitate glands and hairs.

The receptacle of the flower is of moderately long length (about 0.4 to about 0.8 cm.) and of somewhat heavy caliper (about 0.5 to about 0.8 cm. in diameter). The receptacle is urn-shaped to somewhat globular in form. Its surface is very smooth with very few hairs and with somewhat thick fleshy walls. The receptacle color is between 144B and 146B often moderately suffused, especially on the area exposed to the sun, with between 187B and 183B.

As the petals open (after the calyx breaks), the bud is about 1.2 to about 1.6 cm. in diameter at the widest point, about 1.6 to about 2.3 cm. in length, and moderately ovoid to somewhat pointed in form. The color of the under surfaces of the newly opened petals is between 46B and 33A. At the point where the petal attaches, there is a small zone of between 3C and 4B. The color of the upper surfaces of the newly opened petals is between 44B and 33A sometimes lightly blushed on the petal edge with between 187B and 187A. At the point where the petal attaches, there is a moderately small zone of between 5A and 6A.

BLOOM

When fully open, the bloom ranges from about 5.4 to about 6.9 cm. in diameter. Petalage is semi-double with about 12 to 17 petals and about 6 to 11 petaloids irregularly arranged. When partially open, the bloom form is moderately ovoid to somewhat cupped, and the petals are loosely spiraled to cupped with petal edges somewhat reflexed outward. When fully open, the bloom form is cupped and the petals are loosely cupped with petal edges moderately reflexed outward.

PETALS

The substance of the petals is moderately heavy and of somewhat thick thickness, with upper surfaces moderately satiny and under surfaces slightly shiny to matte. The petals are about 2.5 to about 3.2 cm. in length and about 1.8 to about 3.7 cm. in width at the widest point. Petal margins are entire.

The outer petals are moderately obovate to somewhat rounded in shape with rounded apices.

The inner petals are moderately obovate in shape with rounded apices.

Petaloids are about 0.9 to about 3.1 cm. in length and about 0.5 to about 1.8 cm. in width at the widest point. Petaloids are irregularly shaped moderately oblanceolate to somewhat subulate with rounded apices.

NEWLY OPENED FLOWER

The under surface color of the outer, intermediate and inner petals is between 44C and 25A. At the point where the petal attaches, there is a small zone of between 3C and 4B. The upper surface color of the outer, intermediate and inner petals is between 33A and 25A sometimes lightly blushed on the petal edge with between 187B and 187A. At the point where the petal attaches, there is a moderately small zone of between 5A and 6A.

The under and upper surface colors of the petaloids are similar in coloration to the upper and under surfaces of the intermediate and inner petals.

The general tonality of the newly opened flower is between 33A and 25A sometimes lightly blushed on the petal edge with between 187B and 187A.

THREE-DAY-OLD FLOWER

The under surface color of the outer petals is between 44C and 28A. At the point where the petal attaches, there is a small zone of between 3C and 4B. The upper surface color of the outer petals is between 41B and 28A sometimes lightly blushed on the petal edge with between 60B and 59B. At the point where the petal attaches, there is a moderately small zone of between 7C and 6C.

The under surface color of the intermediate and inner petals is between 44C and 28A. The upper surface color of the intermediate and inner petals is between 43B and 28A sometimes lightly blushed on the petal edge with between 60B and 59B.

The under and upper surface colors of the petaloids are similar in coloration to the upper and under surfaces of the intermediate and inner petals.

The general tonality of the three-day-old flower is between 43B and 28A sometimes lightly blushed on the petal edge with between 60B and 59B.

On the spent bloom, the petals usually drop off cleanly.

In October in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 135) and are arranged regularly about the pistils; a few are mixed with petaloids. The filaments are of somewhat short to medium length (about 0.4 to about 0.8 cm.) most with anthers. Filaments are between 12A and 13B in color often moderately suffused with between 53B and 53A. The anthers are of medium size for the class and all open approximately at the same time. Anther color when immature is near 22A on the external part and near 20C on the internal part. Anther color at maturity is near 165B on the external part and near 200A on the internal part. Pollen is abundant and between 18B and 13D in color.

FEMALE REPRODUCTIVE ORGANS

Pistils vary in number (average about 85). The styles are somewhat uneven, average in length (about 0.4 to about 0.7 cm.), moderately thin in caliper, and loosely bunched to somewhat separated. Stigma color is between 18A and 20B. Style color is between 154D and 1D usually heavily suffused with between 187B and 59B. Ovaries are usually all enclosed in the calyx.

Hips are of average length (about 1.4 to about 1.9 cm.), globular in form and between 28B and 30B in color when ripe. The hip surface is smooth with very few stipitate glands and with moderately thick fleshy walls. The sepals are fugacious and usually straight in shape.

The seeds are irregularly rounded, smooth in texture, approximately 13 to about 23 per hip, about 0.3 to about 0.4 cm. in diameter at the widest point and between 161B and 163D in color.

FOLIAGE

The compound leaves are usually comprised of three to seven leaflets and are borne very abundantly. The five-leaflet leaves are about 5.8 to about 10.0 cm. in length and about 4.4 to about 6.9 cm. in width at the widest point, moderately leathery to somewhat crisp in texture, and glossy in finish on the upper side and slightly shiny in finish on the under side. The terminal leaflets are about 2.5 to about 4.2 cm. in length and about 1.6 to about 2.6 cm. in width at the widest point, shaped oval to somewhat ovate with acute apices and rounded to somewhat acute bases. Their margins are usually simply serrate. The venation pattern type is pinnate. The venation coloration of the upper surface is similar to the upper surface color of the mature leaf. The venation coloration of the lower surface is similar to the lower surface color of the mature leaf.

The upper surface color of the mature leaf is between 139A and 137A. The under surface color of the mature leaf is between 147B and 148A. The upper surface color of the young leaf is between 147A and 137A, often heavily suffused with between 187A and 187B. The under surface color of the young leaf is between 146B and 147B, often heavily suffused with between 187A and 187B.

The rachis is moderately light in caliper and rough. The upper side is deeply grooved with few stipitate glands on the edges of the grooves. The under side of the rachis is rough with few stipitate glands and few small prickles. The rachis color is near 146D on the under side and near 137B on the upper side often moderately suffused on the young leaf with between 187A and 187B.

The stipules are about 0.9 to about 1.3 cm. in length and moderately wide (about 0.4 to about 0.6 cm.) with medium length straight points that usually turn out at an angle of more than 45 degrees. The under and upper surface color of the stipule is between 137A and 137B.

The petiole is moderately light in caliper and rough. The upper side is deeply grooved with few stipitate glands on the edges of the grooves. The under side of the petiole is rough with few stipitate glands and few small prickles. The petiole is about 0.6 to about 1.0 cm. in length and about 0.1 to about 0.15 cm in width at the widest point. The petiole color is near 146D on the under side and near 137B on the upper side often moderately suffused on the young leaf with between 187A and 187B.

The plant displays an above average degree of resistance to powdery mildew and rust as compared to other commercial varieties grown under comparable conditions in Wasco, Calif. The plant's winter hardiness and drought/heat tolerance are yet to be determined.

GROWTH

The plant has a bushy upright tall growing habit (about 90 to about 110 cm. in height and about 70 to about 85 cm. spread at the widest point), with very full branching. It displays vigorous growth and the canes are of somewhat heavy caliper for the class (about 1.0 to about 1.4 cm. in diameter at the widest point).

The color of the major stems is between 146A and 146B. They bear many large prickles that are about 0.7 to about 1.2 cm. in length. The large prickles are angled moderately downward with a long somewhat broad oval base; prickle color is between 165B and 164A often lightly suffused with near 201D. The major stem bears few small prickles of similar shape and coloration.

The color of the branches is between 146A and 137B. They bear some large prickles which are of similar shape to the large prickles on the major stems. The large prickles are about 0.5 to about 0.7 cm. in length. Prickle color is near 160A. The branches bear few small prickles of similar shape and coloration.

The color of the new shoots is between 144A and 146B sometimes lightly suffused with between 183A and 187B. They bear some large prickles which are of similar size and shape to the large prickles on the branches; prickle color is near 152D usually heavily suffused with near 187C. The shoots bear few small prickles of similar shape and coloration.

I claim:

1. A new and distinct Miniature rose plant of the variety substantially as described and illustrated herein.

* * * * *

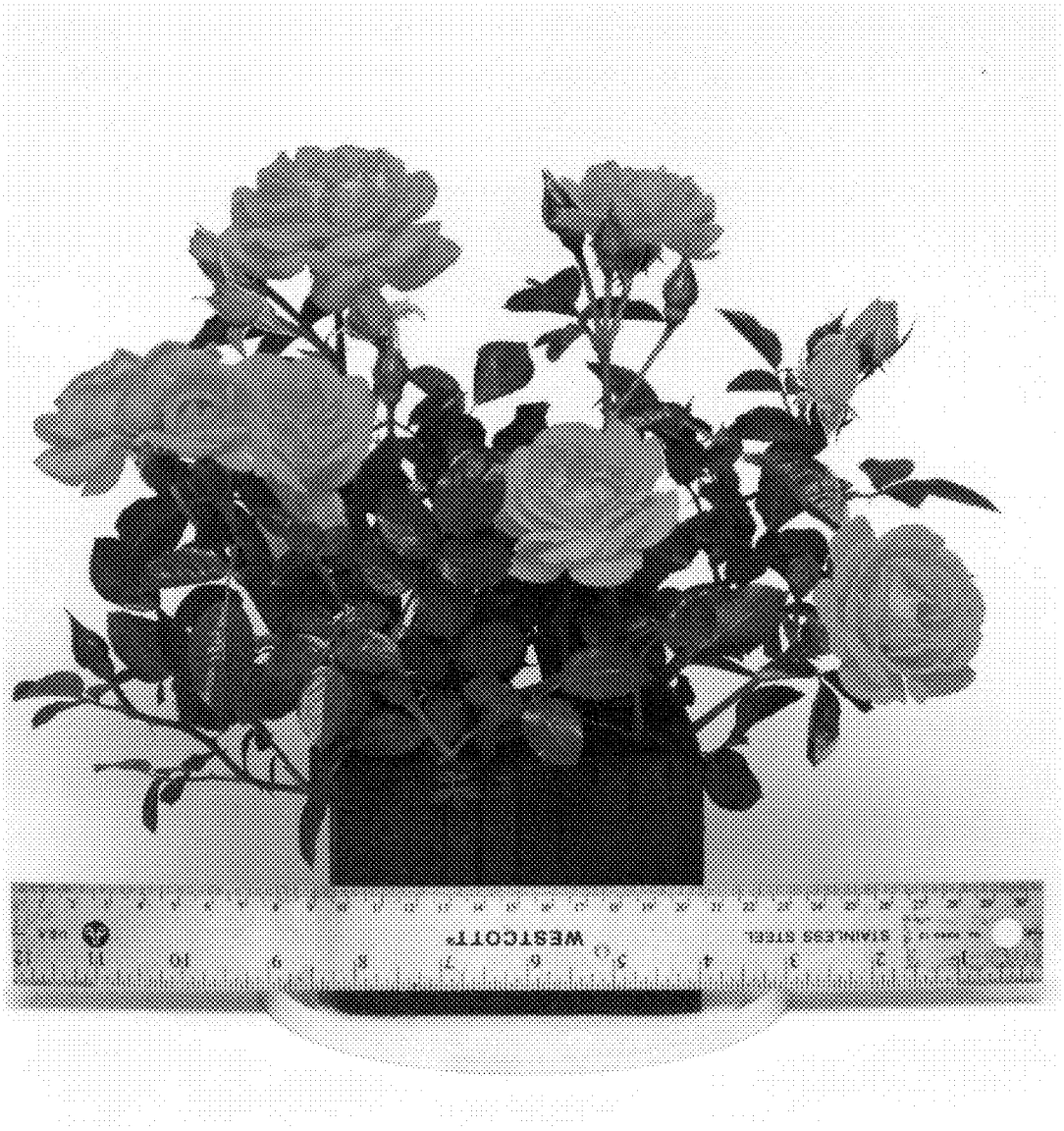
WESTCOTT
STAINLESS STEEL